US012575775B2

(12) United States Patent　　　　(10) Patent No.:　US 12,575,775 B2

Shi　　　　　　　　　　　　　　　　　(45) Date of Patent:　Mar. 17, 2026

(54) INTRA-BODY ELECTRODE WITH A POLY(3,4-ETHYLENEDIOXYTHIOPHENE)-BASED COATING

(71) Applicant: MEDTRONIC, INC., Minnepolis, MN (US)

(72) Inventor: Alan Shi, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 679 days.

(21) Appl. No.: 17/940,771

(22) Filed: Sep. 8, 2022

(65) Prior Publication Data

US 2023/0101016 A1　　Mar. 30, 2023

Related U.S. Application Data

(60) Provisional application No. 63/248,719, filed on Sep. 27, 2021.

(51) Int. Cl.
　　*A61B 5/268*　　　　(2021.01)
　　*A61B 5/00*　　　　(2006.01)

(52) U.S. Cl.
　　CPC ............ *A61B 5/268* (2021.01); *A61B 5/6847* (2013.01); *A61B 2562/125* (2013.01)

(58) Field of Classification Search
　　CPC .. A61B 5/268; A61B 5/6847; A61B 2562/125
　　See application file for complete search history.

(56) References Cited

U.S. PATENT DOCUMENTS

| | | |
|---|---|---|
| 5,131,388 A | 7/1992 | Pless et al. |
| 5,144,949 A | 9/1992 | Olson |
| 5,158,078 A | 10/1992 | Bennett et al. |
| 5,199,428 A | 4/1993 | Obel et al. |
| 5,207,218 A | 5/1993 | Carpentier et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,447,519 A | 9/1995 | Peterson |
| 5,509,411 A | 4/1996 | Littmann et al. |

(Continued)

FOREIGN PATENT DOCUMENTS

| | | |
|---|---|---|
| WO | 2019/152415 | 8/2019 |
| WO | 2021/076054 | 4/2021 |

OTHER PUBLICATIONS

Mandal, H. et al. "Improved Poly(3,4-Ethylenedioxythiophene) (PEDOT) for Neural Stimulation". Neuromodulation: Technology at the Neural Interface. Jan. 27, 2015. (Year: 2015).*

(Continued)

*Primary Examiner* — Eun Hwa Kim
*Assistant Examiner* — William Mossbrook
(74) *Attorney, Agent, or Firm* — Mueting Raasch Group

(57)　　　　ABSTRACT

Embodiments in accordance with the present disclosure are directed to an apparatus comprising an intra-body electrode, and a poly(3,4-ethylenedioxythiophene) (PEDOT)-based coating. The PEDOT-based coating is on a surface of the intra-body electrode. And, the PEDOT-based coating includes a PEDOT-backbone doped with counter ions and cross-linked to a photoreactive polymer and a photoreactive-hydrophilic polymer.

20 Claims, 11 Drawing Sheets

APPARATUS ⌐102

PEDOT-BASED COATING ⌐106

INTRA-BODY ELECTRODE ⌐104

(56)  References Cited

U.S. PATENT DOCUMENTS

| 5,545,186 | A | 8/1996 | Olson et al. | |
|---|---|---|---|---|
| 5,699,796 | A | 12/1997 | Littmann et al. | |
| 5,967,978 | A | 10/1999 | Littmann et al. | |
| 6,021,340 | A | 2/2000 | Randolph et al. | |
| 6,163,723 | A | 12/2000 | Roberts et al. | |
| 6,198,952 | B1 | 3/2001 | Miesel | |
| 8,777,942 | B2 | 7/2014 | Wu et al. | |
| 8,888,773 | B2 | 11/2014 | Chang et al. | |
| 8,998,894 | B2 | 4/2015 | Mauch et al. | |
| 9,037,238 | B2 | 5/2015 | Stadler et al. | |
| 9,370,311 | B2 | 6/2016 | Stewart et al. | |
| 10,245,429 | B2 | 4/2019 | Deem et al. | |
| 10,328,243 | B2 | 6/2019 | Spear et al. | |
| 10,426,377 | B2 | 10/2019 | Markowitz et al. | |
| 10,561,845 | B2 | 2/2020 | Giftakis et al. | |
| 2016/0208114 | A1* | 7/2016 | Hendricks | C09D 5/24 |
| 2020/0377756 | A1 | 12/2020 | Taton et al. | |
| 2021/0345928 | A1* | 11/2021 | Stoica | H01B 1/127 |

OTHER PUBLICATIONS

Extended European Search Report for Application No. 22196944.7 dated Feb. 20, 2023 (8 pages).

Mandal et al., "Improved Poly(3,4-Ethylenedioxythiophene) (PEDOT) for Neural Stimulation", Neuromodulation, vol. 18, No. 8, Dec. 1, 2015, pp. 657-663.

* cited by examiner

320

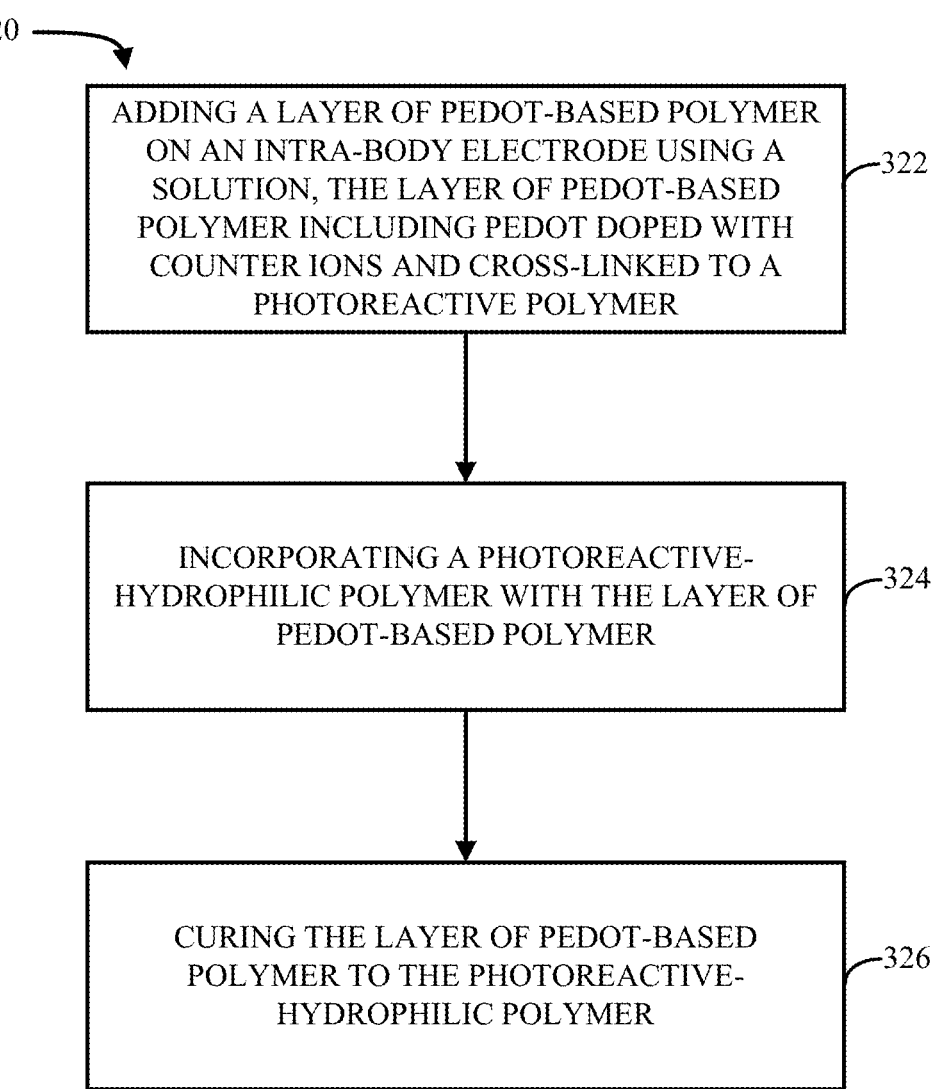

ADDING A LAYER OF PEDOT-BASED POLYMER ON AN INTRA-BODY ELECTRODE USING A SOLUTION, THE LAYER OF PEDOT-BASED POLYMER INCLUDING PEDOT DOPED WITH COUNTER IONS AND CROSS-LINKED TO A PHOTOREACTIVE POLYMER

322

INCORPORATING A PHOTOREACTIVE-HYDROPHILIC POLYMER WITH THE LAYER OF PEDOT-BASED POLYMER

324

CURING THE LAYER OF PEDOT-BASED POLYMER TO THE PHOTOREACTIVE-HYDROPHILIC POLYMER

ELECTRODE CAPACITANCE UNDER CHRONIC STIMULATION
(PTLR CONTROL V. PEDOT COATING AT 45μC/cm²)

BARE PTLR
PEDOT

FIG.12

INTRA-BODY ELECTRODE WITH A POLY(3,4-ETHYLENEDIOXYTHIOPHENE)-BASED COATING

CROSS-REFERENCE TO RELATED APPLICATION

This Non-Provisional Utility Application claims benefit to U.S. Provisional Application No. 63/248,719, filed Sep. 27, 2021, titled "AN INTRA-BODY ELECTRODE WITH A POLY(3,4-ETHYLENEDIOXYTHIOPHENE)-BASED COATING," the entirety of which is incorporated herein by reference.

BACKGROUND

Electrodes form part of and/or are used by various different medical apparatuses for sensing and/or stimulation purposes. In some applications, electrodes can be used in neurological implantable medical apparatuses to sense brainwaves or other biomarkers, and to provide electrical stimulation to tissue. In other applications, electrodes are used in cardiovascular implantable medical apparatuses to sense cardiac signals, and to provide electrical stimulation to nerves and/or tissue. In further example applications, electrodes are used in electrophysiology (EP) mapping medical apparatuses to sense physiological signals inside the heart or through the esophagus and/or ablate tissue based on the sensing.

SUMMARY

The present disclosure is generally directed to apparatuses that include an intra-body electrode with a poly(3,4-ethylenedioxythiophene) (PEDOT)-based coating and methods of forming the intra-body electrode and PEDOT-based coating.

In one aspect, an apparatus includes an intra-body electrode and a PEDOT-based coating. The PEDOT-based coating is on a surface of the intra-body electrode. The PEDOT-based coating includes a PEDOT-backbone doped with counter ions and cross-linked to a photoreactive polymer and a photoreactive-hydrophilic polymer.

In another aspect, an apparatus includes an intra-body electrode and a PEDOT-based coating on a surface of the intra-body electrode. The intra-body electrode with the PEDOT-based coating are configured to provide a capacitance of at least sixty microfarad per square millimeter ($\mu$F/mm$^2$) and to exhibit a relative difference in impedance magnitude at ten kilohertz (kHz) and at ten Hz of five percent or less.

Another aspect is directed to a method of forming an intra-body electrode with a PEDOT-based coating. The method includes adding a layer of a PEDOT-based polymer on an intra-body electrode using a solution. The layer of PEDOT-based polymer includes PEDOT doped with counter ions and cross-linked to a photoreactive polymer. The method includes incorporating a photoreactive-hydrophilic polymer with the layer of PEDOT-based polymer. The method further includes curing the layer of PEDOT-based polymer to the photoreactive-hydrophilic polymer to form a PEDOT-based coating on the intra-body electrode. The PEDOT-based coating includes the PEDOT doped with the counter ions and cross-linked to the photoreactive polymer and the photoreactive-hydrophilic polymer.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 3 is a flowchart illustrating an example method of forming an apparatus including an intra-body electrode with a PEDOT-based coating, in accordance with embodiments of the present disclosure.

FIGS. 10-13 are graphs illustrating example physical properties of intra-body electrodes with a PEDOT-based coating, in accordance with embodiments of the present disclosure.

DETAILED DESCRIPTION

Figure 1:
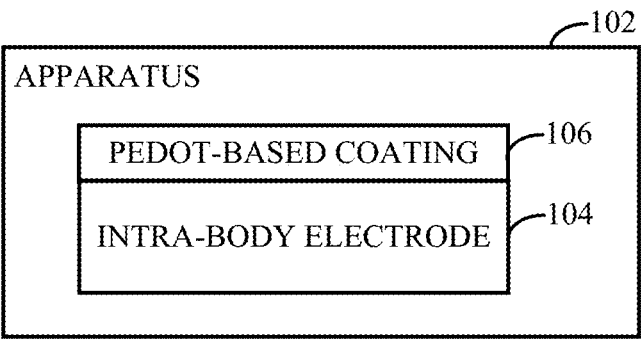
FIG. 1 is a block diagram illustrating an example apparatus including an intra-body electrode with a PEDOT-based coating, in accordance with embodiments of the present disclosure.

Apparatuses and methods embodying principles of the present disclosure can be employed for various types of medical sensing and treatment applications including, but not limited to, neurological, cardiovascular, electrophysiology (EP) sensing and/or stimulation applications. Different medical apparatuses and/or applications can benefit from intra-body electrodes with particular physical properties, such as for electrical stimulation and/or sensing physiological signals. The intra-body electrodes of apparatuses, in accordance with aspects of the present disclosure, can include a PEDOT-based coating on the electrode which includes a PEDOT-backbone doped with counter ions and cross-linked with a photoreactive polymer and a photoreactive-hydrophilic polymer. The PEDOT-based coating can provide various physical properties, such as particular capacitance values, relative differences in impedance, charge storage capacity, and/or electrode potentials, among other properties.

Various medical apparatuses use an electrode for intra-body sensing and/or electrical stimulation purposes, herein generally referred to as an "intra-body electrode". The electrode can be formed of a conductive material, such as platinum, platinum alloys, titanium, titanium alloys, and other biostable metals and alloys. To provide sufficient spatial resolution for sensing and/or stimulation for medical applications, electrodes are increasingly becoming smaller in size. However, when the physical size of the electrodes, and therefore surface area, is too small, (e.g., electrodes of a geometric size on an order of a micrometer ($\mu$m)), the electrodes can possess insufficient intrinsic charge injection capacity to provide and sustain chronic electrical stimulation in a therapeutically effective manner. Further, various medical apparatuses provide both electrical stimulation and sensing, with sensing being used to provide feedback for the electrical stimulation. The physiological signals sensed by the sensing electrode can have amplitudes on an order of microvolts. Due to such amplitudes, the physiological signals can be masked by the electrical stimulation signals provided by the stimulation electrode. In some instances, a coating can be provided on a surface of the electrode to impact electrical stimulation or sensing abilities of the electrode and/or to mitigate corrosion of the intra-body electrode. As the intra-body electrode is exposed to biological material while in-vivo, such as fluid, tissue, and/or a nerve, the coating can degrade overtime which can cause degradation in sensing and/or stimulation performance. For example, PEDOT:polystyrene sulfonate (PSS) coatings can degrade and delaminate over time which can cause a lower life-cycle of the apparatus and/or intra-body electrode. In some embodiments, the intra-body electrode is an implantable electrode which can be implanted, e.g., is implantable, in a patient and/or form part of an implantable medical device. With lower-life cycles, a patient with the intra-body electrode implanted can be subjected to additional surgeries to replace components of the apparatus and/or otherwise cause replacement of the medical procedure apparatus and/or components thereof.

Intra-body electrodes of apparatuses, in accordance with aspects of the present disclosure, can include a PEDOT-based coating on the electrode of a particular size to provide spatially targeted stimulation and/or sensing. The PEDOT-based coating can increase the effective surface area of the electrode, and in response, decrease impedance and enhance charge injection capacity as compared to an electrode without the coating or with other types of coatings. The decrease in impedance can allow for robust sensing of physiological signals by improving coupling between tissue of the patient and the electrode. Enhancements in charge injection capacity can improve electrical stimulation applied to tissue by the intra-body electrode. In some embodiments, the physical properties provided by the PEDOT-based coating can reduce battery consumption, thereby increasing the life-cycle of the apparatus, and/or increase a signal-to-noise ratio for sensing purposes, such as for EP mapping applications, as further described herein. Embodiments are not limited to neurological and/or cardiac applications as described above, and can include, for example, different types of implantable medical apparatuses, medical procedure (e.g., surgical) apparatuses, and sensor apparatuses. As an example, embodiments can include glucose sensing apparatuses and/or drug-delivery apparatuses.

Turning now to the figures, FIG. 1 is a block diagram illustrating an example apparatus including an intra-body electrode with a PEDOT-based coating, in accordance with embodiments of the present disclosure. The apparatus 102 includes the intra-body electrode 104 and the PEDOT-based coating 106 which is on a surface of the intra-body electrode 104. An intra-body electrode, as used herein, includes and/or refers to an electrode that is configured for use within a body of a human or an animal. The intra-body electrode 104 can be implanted within a patient and can form part of an implantable medical device, and/or can be temporarily inserted within the patient and can form part of a medical procedure device.

The intra-body electrode 104 can capture physiological signals, e.g., is a sensing electrode, and/or can provide electrical stimulation, e.g., is a stimulation electrode. Example physiological signals include brainwaves, biomarkers, cardiac signals, and other bioelectrical or chemical signals. In some embodiments, the intra-body electrode 104 can selectively provide both sensing and stimulation.

In some embodiments, the PEDOT-based coating 106 is conductive and includes a PEDOT:tetrafluoroborate (TFB) structure that is cross-linked to a photoreactive polymer and a photoreactive-hydrophilic polymer. The PEDOT-based coating 106 can have a thickness of between approximately one μm to approximately five μm, although examples are not so limited. The chemical structure of the PEDOT-based coating 106 is further described below in connection with FIG. 2.

The PEDOT-based coating 106 can provide a variety of physical properties. For example, the intra-body electrode 104 with the PEDOT-based coating 106 can provide a capacitance of at least sixty microfarad per square millimeter ($g/mm^2$) and can exhibit a relative difference in impedance magnitude at ten kilohertz (kHz) and at ten Hz of five percent or less. The relative difference in impedance can include a percentage, such as $(Z_{10Hz}-Z_{10kHz})/Z_{10kHz}$, that is less than five percent, and in some embodiments, is less than two percent. In some embodiments, the intra-body electrode 104 can achieve a capacitance of at least seventy $\mu F/mm^2$, at least eighty $\mu F/mm^2$, and/or at least one hundred $\mu F/mm^2$. In some embodiments, a capacitance of less than sixty $\mu F/mm^2$ can be achieved by the intra-body electrode 104. The capacitance and/or difference in impedance can allow for coupling between tissue or other body structures and the intra-body electrode 104 that is sufficient to mitigate physiological signal rejection due to noise (e.g., increase the signal-to-noise ratio), such as from an electrical stimulation signal, and can allow for more efficient charge transfer of the electrical stimulation signal to the tissue.

In various embodiments, the intra-body electrode 104 with the PEDOT-based coating 106 can provide a total charge storage capacity of at least four hundred microcoulomb per square millimeter ($\mu C/mm^2$). In some embodiments, the PEDOT-based coating 106 can provide a total charge storage capacity of at least five hundred $\mu C/mm^2$. A charge storage capacity, as used herein, includes and/or refers to a summation of anodic and cathodic charge storage capacity. In some embodiments, the intra-body electrode 104 with the PEDOT-based coating 106 can maintain electrode potentials within a water stability window and minimize electrode polarization under electrical stimuli. The water stability window includes and/or refers to a potential region in which all reactions occurring in water are stable, e.g., no electrolysis occurring. The electrode potential includes and/or refers to a maximum cathode potential (e.g., voltage) and maximum anode potential (e.g., voltage) at particular stimulation or pacing parameters, and can be measured as the potential difference of the maximum cathode potential and maximum anode potential. The electrode potentials being maintained within the water stability window can increase a charge injection capacity of the electrode 104, which can improve stimulation delivery by the intra-body electrode 104. A charge injection capacity, as used herein, includes and/or refers to an amount of charge that can be injected into tissue in a reversible way.

The intra-body electrode 104 can be formed of a variety of conductive materials. For example, the intra-body electrode 104 may be formed from platinum (Pt), platinum/iridium (PtIr), or gold (Au). Other non-limiting example conductive materials can include titanium, titanium alloy, Au alloy, copper coated with Au, among others.

In some embodiments, the intra-body electrode 104, as further illustrated by at least FIG. 5, can be positioned on an exterior surface of an elongate conduit of the apparatus 102, such as an implantable medical device and/or a medical procedure device. For example, the elongate conduit can be a lead that carries a plurality of electrically conductive wires. The electrically conductive wires can extend through the elongate conduit and can connect the intra-body electrode 104 to control circuitry. The lead can have a distal portion that can be positioned near target tissue of the user, with the distal portion including the intra-body electrode 104. The lead can further include a proximal portion positioned near the control circuitry. In some embodiments, such as with ablation catheters, the proximal portion can be coupled to a handle for use in manipulating the elongate conduit. Although embodiments are not so limited, and the intra-body electrode can be in a variety of forms, such as being coupled to a housing of an implantable medical device or forming part of a separate sensor device that is in communication with an implantable medical device to provide sensing and/or electrical stimulation. In some embodiments, the apparatus 102 includes the control circuitry that is in communication with the intra-body electrode 104 which can be used to sense physiological signals and/or to provide electrical stimulation signals to tissue, such as for ablating or electroporation.

In various embodiments, the apparatus 102 includes a plurality of intra-body electrodes including the particular intra-body electrode 104 with the PEDOT-based coating 106. In some embodiments, each of the plurality of intra-body electrodes includes a PEDOT-based coating. In other embodiments, a sub-set of the plurality of intra-body electrodes include the PEDOT-based coating. The plurality of intra-body electrodes can each be configured to capture physiological signals and/or to deliver electrical signals to provide electrical stimulation.

Figure 2:
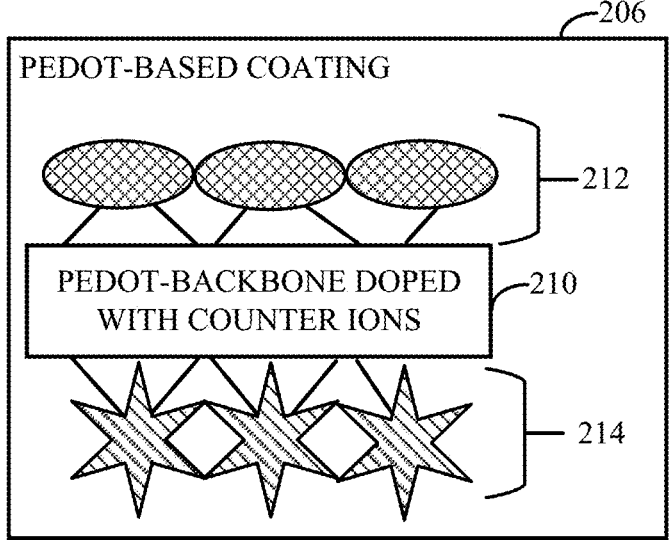
FIG. 2 is a block diagram illustrating an example PEDOT-based coating, in accordance with embodiments of the present disclosure.

FIG. 2 is a block diagram illustrating an example PEDOT-based coating, in accordance with embodiments of the present disclosure. The PEDOT-based coating 206 of FIG. 2 can include the PEDOT-based coating 106 and/or be implemented on the intra-body electrode 104 of FIG. 1 in various embodiments. In some embodiments, the PEDOT-based coating 206 can be a layer on an implantable electrode, which can form part of or be in communication with an implantable medical device.

As shown by FIG. 2 the PEDOT-based coating 206 can include a PEDOT-backbone 210 doped with counter ions. The PEDOT-backbone 210, as used herein, includes and/or refers to a chain of covalently bonded 3,4-ethylenedioxy-thiophene (EDOT) monomers. The counter ions can be attached to (e.g., hanging onto) the PEDOT-backbone 210 via coulombic interactions. The counter ions can maintain a charge neutrality of the PEDOT-backbone 210. In some embodiments, the counter ions can be negatively charged and/or include a negatively charged functional group. In some embodiments, the counter ions include TFB and the PEDOT-backbone 210 doped with counter ions can include or form a PEDOT:TFB structure. The PEDOT-backbone 210 can be cross-linked to a photoreactive polymer 212 and a photoreactive-hydrophilic polymer 214. For example, a PEDOT:TFB structure can be cross-linked to the photoreactive polymer 212 and the photoreactive-hydrophilic polymer 214. Cross-linked, as used herein, includes and/or refers to a covalent linkage between two components (e.g., two polymers or a polymer and counter ions), or between different regions of the same polymer.

The photoreactive polymer 212 can be non-charged (e.g., is non-ionic) and can provide passivation against protein and cell adhesion when the intra-body electrode, such as the intra-body electrode 104 illustrated by FIG. 1, is implanted or otherwise in-vivo. In some embodiments, the photoreactive polymer 212 can provide metal adhesion to the PEDOT-based coating 206 and/or is water soluble and/or hydrophilic. A photoreactive polymer includes and/or refers to a polymer that changes properties when exposed to light, such as cross-linking when exposed to light.

The photoreactive polymer 212 can be formed of a variety of different polymers and photoreactive groups, such as different monomers, oligomers, and/or photoinitiators. Example photoreactive groups include aryl ketones, azides, diazos, diazirines, ketones, and quinones. The photoreactive groups generate active species including, for example, nitrenes, carbenes, and excited states of ketones upon absorption of electromagnetic energy from light. In some examples, the monomers can include styrene, N-Vinylpyr-rolidone, acrylates, diamines, diisocyanates, amines, isocyanate, siloxane, and various combinations thereof. Example photoreactive polymers include styrene and acrylates, poly (aryl ether ketone), silicone-based polymers, ISurTec ISur-Glide® Coating Solution 460.45 (Innovative Surface Technologies, Inc., St. Paul, Minn.), ISurTec ISurGlide® Plus Coating Solution 463.45 (Innovative Surface Technologies, Inc., St. Paul, Minn.), and a synthesized chemical from ISurTec (Innovative Surface Technologies, Inc., St. Paul, Minn.) that includes a polymer having at least some of substantially the same features and attributes as a polymer disclosed in U.S. Patent Publication No. 2020/0377756. Other example polymers and/or components of the polymers can include silicone, hydrocarbons, polyethylene glycol, polypropylene glycol, dipiperidyl propane, among other polymers and copolymers thereof that are linked by a linking group, such as a urea group. In some embodiments, the photoreactive polymer 212 includes copolymers formed of silicone isocyanate, diamines, and diisocyanates, such as silicone polyurea copolymers including siloxane, alkyl, and polyethylene glycol/polypropylene glycol copolymer or dipiperidyl propane repeating units which are separated by urea linkages. In specific examples, the photoreactive polymer 212 includes a polymer having at least some of substantially the same features and attributes as a polymer, such as from example 26, 27, 29 or 30, as described in U.S. Patent Publication No. 2020/0377756, published on Dec. 3, 2020, and entitled "POLYUREA COPOLYMER COMPOSITIONS AND METHODS", which is hereby incorporated by reference in its entirety for its general teachings on polymers and specific teachings related to example polymers as described at least by examples 26, 27, 29, and 30.

The photoreactive-hydrophilic polymer 214 can be partially cross-linked to the PEDOT-backbone 210 and can form a layer on the PEDOT-based coating 206. The photoreactive-hydrophilic polymer 214 is both photoreactive and hydrophilic. In some embodiments, the photoreactive-hydrophilic polymer 214 is neither anionic or cationic (e.g., is non-ionic) in that when the photoreactive-hydrophilic polymer 214 is cured, the photoreactive-hydrophilic polymer 214 has no permanent charge. For example, the photoreactive-hydrophilic polymer 214 can be non-charged. The photoreactive-hydrophilic polymer 214 can be a hydrogel that provides lubricity (e.g., reduce friction) and wettability to the PEDOT-based coating 206 on the surface of the intra-body electrode, such as the intra-body electrode 104 of FIG. 1. For example, the photoreactive-hydrophilic polymer 214 may swell in the presence of water to provide lubricity. Hydrophilic, as used herein, includes and/or refers to a compound which is attracted to or absorbs water. The photoreactive-hydrophilic polymer 214 can create an outer aqueous environment, which creates a more biocompatable surface chemistry.

The photoreactive-hydrophilic polymer 214 can be formed of a variety of different polymers, photoreactive groups, and/or linking groups, such as different monomers, oligomers, and/or photoinitiators. Example photoreactive-hydrophilic polymers include polyvinylpyrrolidone, poly-acrylamide, hyaluronic acid, polylactic acid, polyethylene glycol, collagen, and chitosan. In some embodiments, the photoreactive-hydrophilic polymer 214 can include photo-reactive groups, as described above, and/or linking groups, such as urea, glycol, triazine, polyalcohol, uracil, tetraeth-ylene glycol, hexaethylene glycol, among others. Specific examples of the photoreactive-hydrophilic polymer 214 include Harland Medical Systems Lubricent® (Harland Medical Systems, Inc., Eden Prairie, Minn.), Surmodics Serene™ lubricious coating (Surmodics, Inc., Eden Prairie, Minn.), AST Products LubriLast™ lubricious coating (AST Products, Inc., Billerica Mass.), ISurTec ISurGlide® Coat-ing Solution 460.45 (Innovative Surface Technologies, Inc., St. Paul, Minn.), ISurTec ISurGlide® Plus Coating Solution 463.45 (Innovative Surface Technologies, Inc., St. Paul, Minn.), and DSM Comfortcoat® lubricious coating (DSM Biomedical, Inc., Exton, Pa.). In some examples, the pho-toreactive-hydrophilic polymer 214 includes ISurTec ISur-Glide® Coating Solution 460.45 (Innovative Surface Tech-nologies, Inc., St. Paul, Minn.) or ISurTec ISurGlide® Plus Coating Solution 463.45 (Innovative Surface Technologies, Inc., St. Paul, Minn.), with the numbers 460.45 and 463.45 including IsSurTec product number codes. In some examples, the photoreactive-hydrophilic polymer 214 (and/ or the photoreactive polymer 212) includes a polymer hav-ing at least some of substantially the same features and attributes as a polymer, as described in: U.S. Pat. No. 7,772,393, granted on Aug. 10, 2010, and entitled "PHO-TOCHEMICAL CROSSLINKERS FOR POLYMER COATINGS AND SUBSTRATE TIE-LAYER"; and U.S. Patent Publication No. 2020/0405909, published on Dec. 31, 2020, and entitled "SILCONE POLYUREA BLOCK COPOLYMER COATING COMPOSITIONS AND METH-ODS", each of which are hereby incorporated in their entirety for their general and specific teachings on polymers.

The combination of the PEDOT-backbone 210 doped with the counter ions (e.g., the PEDOT:TFB structure) and the cross-linked photoreactive polymer 212 and the photo-reactive-hydrophilic polymer 214 can provide the PEDOT-based coating 206 that is chemically and mechanically stable when in-vivo. The PEDOT-based coating 206 can be mechanically durable, and can mitigate or prevent degrada-tion of electrode performance, such as for electrical stimu-lation or sensing.

FIG. 3 is a flowchart illustrating an example method of forming an apparatus including an intra-body electrode with a PEDOT-based coating, in accordance with embodiments of the present disclosure. The method 320 can be imple-mented to form the apparatus 100 illustrated by FIG. 1 and/or to form an apparatus that includes an intra-body electrode with a PEDOT-based coating 206 as illustrated by FIG. 2.

At 322, the method 320 includes adding a layer of PEDOT-based polymer on an intra-body electrode using a solution. The layer of PEDOT-based polymer can include PEDOT (e.g., a PEDOT-backbone) doped with counter ions and cross-linked to a photoreactive polymer, such as the photoreactive polymer 212 as previously described by FIG. 2. In some embodiments, the layer of PEDOT-based polymer includes a PEDOT-backbone doped with the TFB as counter ions and cross-linked to the photoreactive polymer, such a PEDOT:TFB structure cross-linked to the photore-active polymer.

In some embodiments, the solution includes EDOT mono-mer, the photoreactive polymer, the counter ions, and a solvent. For example, the method 320 can further include forming the solution by dissolving a volume of the EDOT monomer in the solvent. In some embodiments, the solution can include tetrabutylammonium tetrafluoroborate (TBATFB), the counter ions that include TFB, and the solvent that includes acetonitrile.

In various embodiments, adding the layer of PEDOT-based polymer includes electrochemically depositing PEDOT doped with counter ions (e.g., a layer) on a surface of the intra-body electrode using the solution. After the electrochemical deposition, the PEDOT doped with counter ions can include a PEDOT:TFB structure that passively incorporates the photoreactive polymer. As further illus-trated and described by the method 440 of FIG. 4, electro-chemically depositing the layer can include depositing the PEDOT doped with counter ions using potentiostatic elec-trochemical deposition by applying a voltage (verses satu-rated calomel reference electrode (SCE)) for a period of time to the intra-body electrode while the intra-body electrode is submerged in the solution. In some embodiments, the volt-age can be applied across a voltage range and at a scan rate. For example, the electrochemical deposition can be applied via cyclic voltammetry (CV) between a voltage range and at a scan rate for a number of cycles. In some embodiments, a CV is run for five cycles from a voltage range of −0.6 V to 1.6. V SCE at a scan rate of 50 millivolts per second (mV/s) while the intrabody electrode is submerged in the solution. Adding the layer can further include curing the PEDOT doped with the counter ions (e.g., the PEDOT:TFB struc-ture) to the passively incorporate photoreactive polymer to form the layer of PEDOT-based polymer including the PEDOT doped with counter ions cross-linked to the photo-reactive polymer. For example, the PEDOT doped with the counter ions and the passively incorporated photoreactive polymer can be exposed to ultraviolet (UV) light for a period of time. Exposing the passively incorporated photoreactive polymer to the UV light can cure the photoreactive polymer, resulting in the photoreactive polymer being cross-linked to the PEDOT doped with counter ions, which can improve the mechanical durability of the resulting PEDOT-based coat-ing, and mitigate the risk of corrosion/dissolution and/or the risk of electrolysis occurring when the intra-body electrode is in-vivo. Prior to curing the photoreactive polymer to the PEDOT doped with counter ions, the PEDOT doped counter ions can itself form a layer of polymer that has inadequate mechanical durability and which may shed.

At 324, the method 320 includes incorporating a photo-reactive-hydrophilic polymer with the layer of PEDOT-based polymer, such as the photoreactive-hydrophilic poly-mer 214 as previously described by FIG. 2. In some embodiments, incorporating the photoreactive-hydrophilic polymer with the layer of PEDOT-based polymer includes dip coating the intra-body electrode with the layer of PEDOT-based polymer in a solution that includes the pho-toreactive-hydrophilic polymer dissolved in a solvent. For example, the solution can include Isopropanol and the photoreactive-hydrophilic polymer.

At 326, the method 320 further includes curing the layer of PEDOT-based polymer to the photoreactive-hydrophilic polymer to form a PEDOT-based coating on the intra-body electrode. Curing the layer of PEDOT-based polymer to the photoreactive-hydrophilic polymer can include exposing the layer of PEDOT-based polymer, e.g., the PEDOT:TFB structure, with the incorporated photoreactive-hydrophilic polymer on the intra-body electrode to UV light for a period of time. As previously described, the PEDOT-based coating includes the PEDOT doped with the counter ions and cross-linked to the photoreactive polymer and the photoreactive-hydrophilic polymer. In specific embodiments, the resulting PEDOT-based coating includes a PEDOT:TFB structure cross-linked to the photoreactive polymer and the photoreactive-hydrophilic polymer, such as previously described by FIG. 2.

The method 320 can include a number of variations and/or additional steps. For example, the method 320 can include an additional curing step. In some embodiments, after adding the layer of PEDOT-based polymer, at 322, and before incorporating the photoreactive-hydrophilic polymer, at 324, the method 320 can include curing an additional amount of the photoreactive polymer to the layer of PEDOT-based polymer. For example, the PEDOT:TFB structure cross-linked to the photoreactive polymer can be dip coated in a solution including the photoreactive polymer (to add an additional amount of the photoreactive polymer) and cured using UV light. However, embodiments are not so limited.

As another example variation to the method 320, the apparatus can include a plurality of intra-body electrodes. Each of the plurality of intra-body electrodes can be coated at the same time using the above example method 320. In other embodiments, a sub-set of the plurality of intra-body electrodes can be coated and the remaining intra-body electrodes of the plurality can be uncoated. Each of the plurality of intra-body electrodes can be separately controlled using electrically conductive wires coupled to the intra-body electrodes. For example, the electric potential of each of the plurality of intra-body electrodes can be controlled separately, such as by control circuitry. In some embodiments, all of the intra-body electrodes can be driven to control the potential of the intra-body electrodes and to cause each of the intra-body electrodes to include a layer of the PEDOT-based polymer after the electrochemical deposition. In some embodiments, the sub-set of the plurality of intra-body electrodes are driven, resulting in the sub-set of intra-body electrodes having the layer of the PEDOT-based polymer, and the non-driven intra-body electrodes to not have the layer of PEDOT-based polymer. The subsequent dip coating processes can result in binding of photoreactive-hydrophilic polymer to the layer of PEDOT-based polymer, and binding of the photoreactive-hydrophilic photoreactive polymer and/or additional photoreactive polymer to the bare electrode material, with the performance of the electrode not being compromised. In some embodiments, the electrodes (without the layer of PEDOT-based polymer) can have a layer of the photoreactive-hydrophilic polymer having a thickness on an order of a sub-μm.

Figure 4:
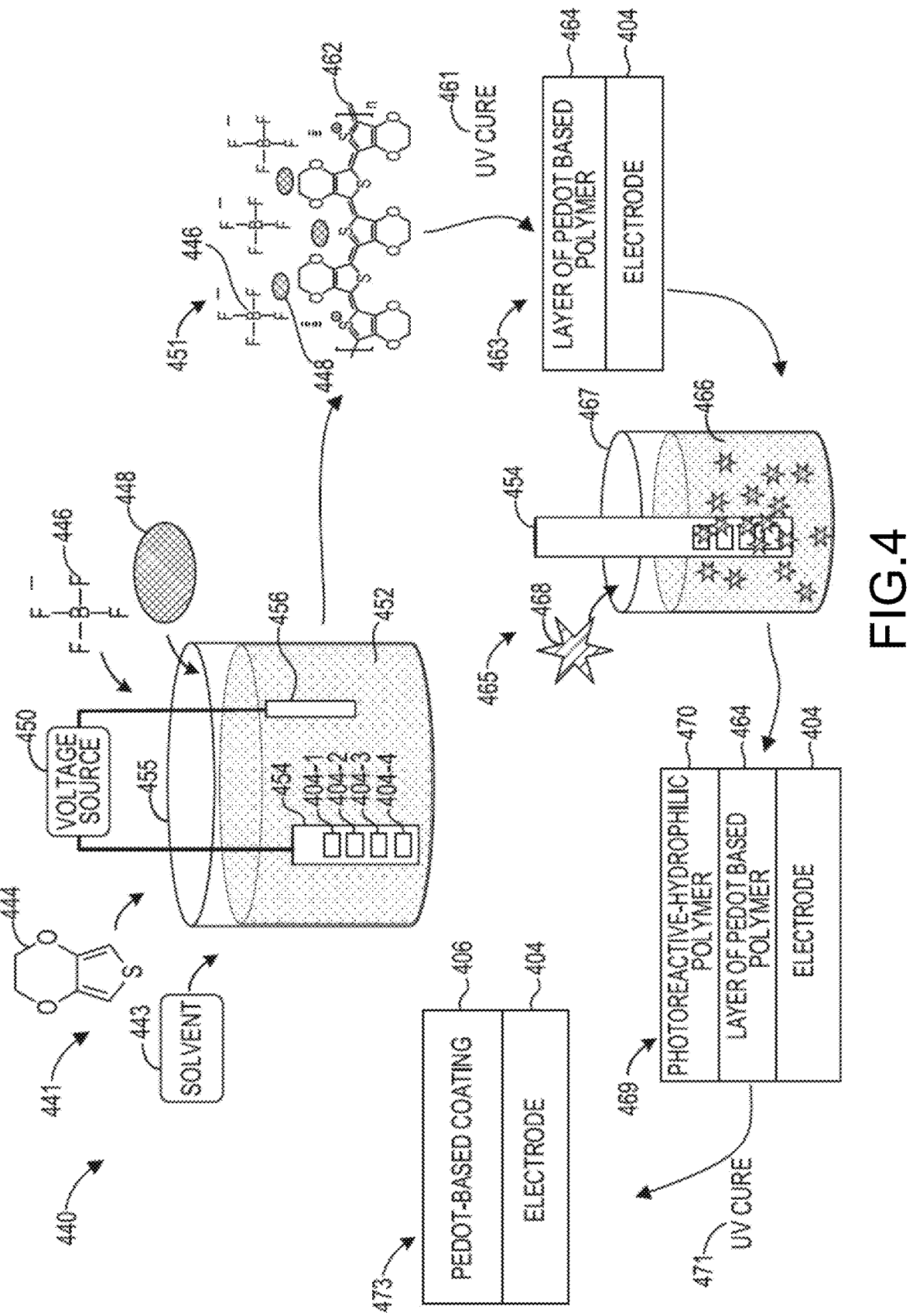
FIG. 4 is a flowchart illustrating another example method of forming an apparatus including an intra-body electrode with a PEDOT-based coating, in accordance with embodiments of the present disclosure.

FIG. 4 is a flowchart illustrating another example method of forming an apparatus including an intra-body electrode with a PEDOT-based coating, in accordance with embodiments of the present disclosure. In some embodiments, the method 440 of FIG. 4 can include an example implementation of the method 320 previously described by FIG. 3.

At 441, the method 440 includes performing an electrochemical deposition on at least a portion of an apparatus 454 that includes at least one intra-body electrode 404-1, 404-2, 404-3, 404-4. In some embodiments, the apparatus 454 includes an array of intra-body electrodes 404-1, 404-2, 404-3, 404-4. Although four intra-body electrodes 404-1, 404-2, 404-3, 404-4 are illustrated, embodiments are not so limited and example apparatuses can include a variety of different numbers of electrodes.

The electrochemical deposition can involve a solution 452 and three electrodes, referred to as the working electrode (WE), the counter electrode (CE) 456, and the reference electrode (RE). The solution 452 includes EDOT monomers 444, a solvent 443, counter ions of TFB 446, and a photoreactive polymer 448 (e.g., the photoreactive groups forming the polymer 448). In some embodiments, the solvent 443 includes an organic solvent, such as Acetonitrile, in which the EDOT monomers 444, TFB 446, and photoreactive polymer 448 are dissolved to form the solution 452 for deposition. For example, the solution 452 can include EDOT monomers 444, TBATFB, and photoreactive polymer 448 in Acetonitrile. In some embodiments, the solution 452 can include 0.001 Moles (M) to 1 M EDOT, 0.01 M to 0.2 M TBATFB, and 1 to 5 milligram per milliliter (mg/mL) photoreactive polymer 448 in Acetonitrile. In some embodiments, the solution 452 includes 0.01 M EDOT, 0.1 M TBATFA, and 1 mg/mL photoreactive polymer 448 in Acetonitrile.

During electrodeposition, the intra-body electrodes 404-1, 404-2, 404-3, 404-4 of the apparatus 454 act as the WE and exchange electrons with the solution 452 to activate the EDOT monomers 444. The CE 456 closes the electrical circuit and allows for current to flow in the intra-body electrodes 404-1, 404-2, 404-3, 404-4, which are acting as the WE. The CE 456 can be made of Pt, in some specific examples. The RE possesses known electrochemical potential, which can be used as a reference for the potentials. Example REs include SCE and Ag/AgCl electrode.

To perform the electrochemical deposition, the apparatus 454 and CE 456 can be submerged into a container 455 that contains the solution 452. A potential can be applied at the WE using the voltage source 450, and the EDOT monomers 444 can undergo an electropolymerization process (while in the presence of the photoreactive polymer 448), forming a porous PEDOT polymer film (e.g., the PEDOT:TFB structure which passively incorporates the photoreactive polymer 448) at the surface of the WE. The polymer can continue to grow, so long as current is supplied or dissolved monomers are available, as shown by the PEDOT-backbone 462.

The electrochemical deposition can include a potentiostatic electrochemical deposition, galvanostatic electrochemical deposition, or a potentiodynamic electrochemical deposition. A potentiostatic deposition can include the application of a constant potential at the WE for a certain amount of time. A galvanostatic deposition can include the application of a constant current instead of a constant potential. For a potentiodynamic deposition, the potential can be swept across a potential window at a specific scan rate multiple times. In some embodiments, a potentiostatic electrochemical deposition is applied at 1.3 V verses SCE for between one hundred fifty to six hundred seconds at room temperature. In some embodiments, the 1.3 V verses SCE is applied for four hundred seconds, and in other examples, is applied for greater than six hundred seconds. In some embodiments, the potentiodynamic electrochemical deposition can be applied via CV between a voltage range and at a scan rate for a number of cycles, such as between −0.6 V to 1.6. V SCE at 50 mV/s for five cycles while the intrabody electrode is submerged in the solution.

After the electrochemical deposition, as shown at 451, a PEDOT-backbone 462 is formed that includes PEDOT doped with the counter ions of TFB 446 (as illustrated by the particular TFB ion labeled by 446). The PEDOT-backbone 462 doped with the TFB 446 further includes the photoreactive polymer 448 (as illustrated by the particular photo-reactive polymer group labeled by 448) that is passively incorporated with the PEDOT:TFB structure. In this manner, the PEDOT-backbone 462 and TFB 446 form a PEDOT:TFB structure.

At 461, the PEDOT-backbone 462 doped with the TFB 446 is cured to the passively incorporated photoreactive polymer 448 via UV light. In some specific embodiments, the PEDOT-backbone 462 doped with TFB 446 can be UV cured for one to five minutes. As shown at 463, curing the photoreactive polymer 448 can form the layer of PEDOT-based polymer 464 on the intra-body electrode 404. The layer of PEDOT-based polymer 464 includes the PEDOT:TFB structure (e.g., formed by PEDOT-backbone 462 and TFB 446) that is cross-linked to the photoreactive polymer 448. The intra-body electrode 404 can include any of the intra-body electrodes 404-1, 404-2, 404-3, 404-4 illustrated at 441. Although only one electrode is illustrated, as described above, multiple electrodes can be coated at the same time by controlling the potentials of the intra-body electrodes 404-1, 404-2, 404-3, 404-4.

Although not illustrated by FIG. 4, in some embodiments, the method 440 can further include adding an additional amount of the photoreactive polymer 448 to the layer of PEDOT-based polymer 464. For example, after curing at 461, the method 440 can include adding the additional amount of the photoreactive polymer 448 by dip coating the apparatus 454 in a solution that includes the photoreactive polymer 448 dissolved in a solvent and curing the additional amount of the photoreactive polymer 448. In some embodiments, the solution includes between ten to fifty mg/mL of the photoreactive polymer 448 in water, which the apparatus 454 is submerged in for between ten to sixty seconds and removed (e.g., pulled up) from the solution, and then UV cured for between one to five minutes. In some embodiments, the solution includes fifty mg/mL of the photoreactive polymer 448 in water, and the apparatus 454 is submerged in the solution for thirty seconds and removed (e.g., pulled up) from the solution, and then UV cured for five minutes. The additional amount of the photoreactive polymer 448 can be coated on the layer of PEDOT-based polymer 464 as illustrated by the intra-body electrode 404, which cross-links with the PEDOT:TFB structure after curing.

At 465, the method 440 includes incorporating a photo-reactive-hydrophilic polymer 468 with the layer of PEDOT-based polymer 464 via a dip coating process. For example, the apparatus 454 can be submerged, at least partially, into a container 467 that contains a solution 466. The solution 466 includes the photoreactive-hydrophilic polymer 468 (e.g., monomers forming the polymer 468) dissolved in a solvent. In some embodiments, the solution 466 includes the photoreactive-hydrophilic polymer 468 dissolved in Isopropanol, such as 4.5 weight percentage of the photoreactive-hydrophilic polymer 468 dissolved in Isopropanol. The apparatus 454 can be submerged in the solution 466 for between ten to sixty seconds and then air dried. In some embodiments, the apparatus 454 is submerged in the solution 466 for thirty seconds and then air dried. After dip coating to incorporate the photoreactive-hydrophilic polymer 468, as shown at 469, the intra-body electrode 404 can include the layer of PEDOT-based polymer 464 with a layer of the photoreactive-hydrophilic polymer 470.

At 471, the method 440 includes curing the layer of photoreactive-hydrophilic polymer 470 to the layer of PEDOT-based polymer 464 using UV light for a period of time, such as one to five minutes. As shown at 473, after curing, a PEDOT-based coating 406 is formed on the intra-body electrode 404. In some embodiments, the PEDOT-based coating 406 includes the PEDOT:TFB structure that is cross-linked to the photoreactive polymer 448 and the photoreactive-hydrophilic polymer 468. The PEDOT:TFB structure being cross-linked to the photoreactive-hydrophilic polymer 468 can include a complete cross-link or a partial cross-link, with the photoreactive-hydrophilic polymer 468 forming an additional layer on the PEDOT:TFB structure. In some embodiments, experiments were conducted to test formation of example intra-body electrodes with the PEDOT-based coating. The electrode included a PtIr electrode that was submerged in a solution including 0.01 M EDOT, 0.1 M TBATFB, and 1 mg/mL photoreactive polymer (e.g., a synthesized chemical from ISurTec (Innovative Surface Technologies, Inc., St. Paul, Minn.) which includes a polymer having at least some of substantially the same features and attributes as any polymer disclosed in U.S. Patent Publication No. 2020/0377756, such as examples 26, 27, 29, and/or 30) in Acetonitrile. While submerged, a potentiostatic electrochemical deposition was applied at 1.3 V verses SCE for four hundred seconds at room temperature. The potentiostatic electrochemical deposition resulted in a layer of PEDOT-backbone doped with TFB that passively incorporated the photoreactive polymer. The layer was exposed to UV light for five minutes to cure the photoreactive polymer and form a PEDOT:TFB structure cross-linked to the photoreactive polymer. The electrode with the PEDOT:TFB structure cross-linked to the photoreactive polymer was dip coated in fifty mg/mL photoreactive polymer (e.g., a synthesized chemical from ISurTec (Innovative Surface Technologies, Inc., St. Paul, Minn.) including at least some of substantially the same features and attributes as any polymer disclosed in US Publication No. 2020/0377756) in water for thirty seconds, air dried, and then UV cured for five minutes. The electrode with the PEDOT:TFB structure cross-linked to the photoreactive polymer was then dip coated in a solution of 4.5 weight % dissolved solid photoreactive-hydrophilic polymer (e.g., ISurTec ISurGlide® Coating Solution 460.45 (Innovative Surface Technologies, Inc., St. Paul, Minn.) or ISurTec ISurGlide® Plus Coating Solution 463.45 (Innovative Surface Technologies, Inc., St. Paul, Minn.)) solution in Isopropanol for thirty seconds and UV cured for five minutes.

Various embodiments are directed to an intra-body electrode with a PEDOT-based coating, which can be used in a variety of different medical apparatuses and for a variety of medical purposes. The PEDOT-based coating is conductive and provides improved charge injection capacity, reduced pacing after-polarization, improved signal-to-noise ratio, improved amplitude of sensed physiological signals, and increased life of the apparatus, as described above.

FIGS. 5A-8 are diagrams illustrating example apparatuses including an intra-body electrode with a PEDOT-based coating. As described above, example intra-body electrodes can be used in a variety of medical apparatus and for a variety of applications. In some embodiments, the intra-body electrode is an implantable electrode forming part of or otherwise in communication with an implantable medical device, and that is implantable in a patient. However examples are not so limited, and in some embodiments, the intra-body electrode forms part of a medical procedure device.

Figure 5A:
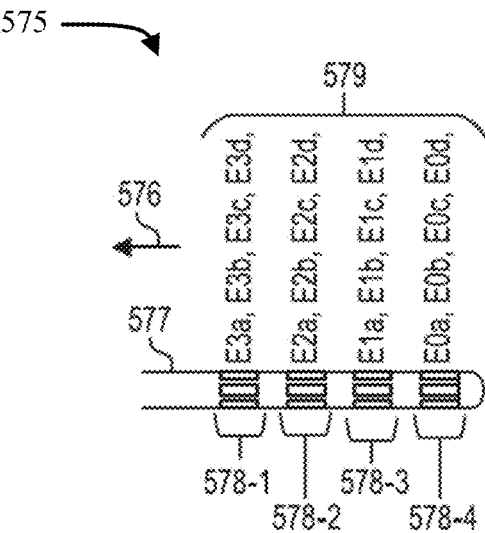
FIGS. 5A-8 are diagrams illustrating example apparatuses including an intra-body electrode with a PEDOT-based coating, in accordance with embodiments of the present disclosure.

FIG. 5A illustrates an example of a neurological apparatus 575 that includes an intra-body electrode with a PEDOT-based coating, in accordance with embodiments of the present disclosure. In some embodiments, the neurological apparatus 575 of FIG. 5A can include a deep brain stimulation device. For neurological implementations, an array of intra-body electrodes 578-1, 578-2, 578-3, 578-4 can be used to record neural recordings and/or to provide electrical stimulation. Electrodes of a size on a magnitude of μm can allow for multiple electrodes to be spaced on an elongate conduit 577 (e.g., a lead), which can improve spatial targeting selectivity and minimize side effects from the electrical stimulation. In various embodiments, one or more of the electrodes of the array of intra-body electrodes 578-1, 578-2, 578-3, 578-4 can have a PEDOT-based coating, and in some embodiments, each of the intra-body electrodes of the array 578-1, 578-2, 578-3, 578-4 can have the PEDOT-based coating.

The neurological apparatus 575 can include an elongate conduit 577 having a distal portion 579 that is positionable with tissue of a patient and a proximal portion 576 which can be coupled to control circuitry. Electrical wires can be positioned within the elongate conduit 577 and can couple the control circuitry to the electrodes. The array of intra-body electrodes 578-1, 578-2, 578-3, 578-4 can be positioned on the distal portion 579. In some embodiments, the array of intra-body electrodes 578-1, 578-2, 578-3, 578-4 includes four sets of four electrodes that are positioned about a circumference of the elongate conduit 577, as shown by the notations of (E0a, E0b, E0c, E0d), (E1a, E1b, E1c, E1d), (E2a, E2b, E2c, E2d), and (E3a, E3b, E3c, E3d).

Figure 5B:
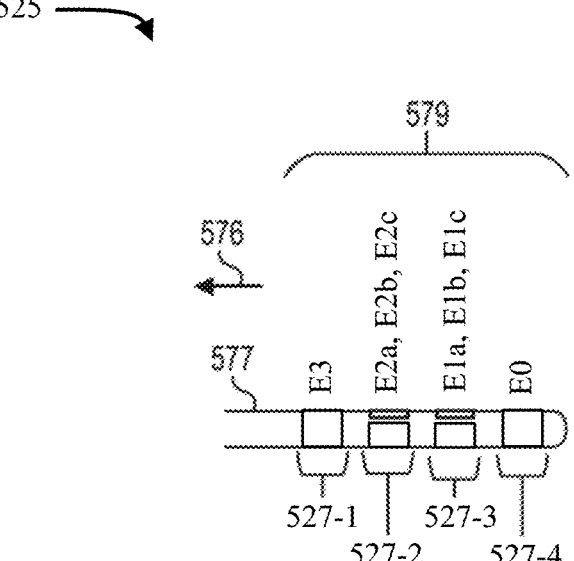

FIG. 5B illustrates another example of a neurological apparatus 525 that includes an intra-body electrode with a PEDOT-based coating, in accordance with embodiments of the present disclosure. In some embodiments, the neurological apparatus 525 of FIG. 5B can include a deep brain stimulation device. For neurological implementations, an array of intra-body electrodes 527-1, 527-2, 527-3, 527-4 can be used to record neural recordings and/or to provide electrical stimulation. As described in connection with FIG. 5A, electrodes of a size on a magnitude of μm can allow for multiple electrodes to be spaced on an elongate conduit 577 (e.g., a lead), which can improve spatial targeting selectivity and minimize side effects from the electrical stimulation. In various embodiments, one or more of the electrodes of the array of intra-body electrodes 527-1, 527-2, 527-3, 527-4 can have a PEDOT-based coating, and in some embodiments, each of the intra-body electrodes of the array 527-1, 527-2, 527-3, 527-4 can have the PEDOT-based coating.

The neurological apparatus 525 can include an elongate conduit 577 having a distal portion 579 that is positionable with tissue of a patient and a proximal portion 576 which can be coupled to control circuitry. Electrical wires can be positioned within the elongate conduit 577 and can couple the control circuitry to the electrodes. The array of intra-body electrodes 527-1, 527-2, 527-3, 527-4 can be positioned on the distal portion 579. In some embodiments, the array of intra-body electrodes 527-1, 527-2, 527-3, 527-4 includes an arrangement of one electrode, three electrodes, three electrodes, and one electrode that are positioned about a circumference of the elongate conduit 577, as shown by the notations of (E0), (E1a, E1b, E1c), (E2a, E2b, E2c), and (E3).

For the neurological apparatus 575, 525 of FIGS. 5A-5B, the entire electrode array and spacing between respective electrodes can be on a range of μm, such an array of ten μm or less and a spacing of five μm or less between electrodes. For neuromodulation, the size of the electrodes and the PEDOT-based coating can allow for a high aspect ratio to provide a high bandwidth tissue-to-electrode interface for both sensing brainwaves or other physiological signals, and for providing electrical stimulation.

As described above, the PEDOT-based coating can be used on the sensing electrodes in the neurological apparatus 575, 525 to create an impedance interface between the sensing electrodes and the tissue that is sufficient to sense brainwaves (and other physiological signals) without or while minimizing interference from electrical stimulation provided by the stimulation electrodes. In some embodiments, the sensing electrode with the PEDOT-based coating can be used to sense local field potentials (LFP), such as for guiding deep brain stimulation (DBS) intraoperative procedures. The PEDOT-based coating can additionally or alternatively be used on stimulation electrodes to create an impedance interface between the stimulation electrodes and the tissue that is sufficient to deliver therapy to the tissue while keeping the electrodes μm sized. As described above, the PEDOT-based coating can minimize electrode/tissue impedance, enable electrodes of a size in the μm range while allowing for an effective surface area that is sufficient to deliver therapy to the tissue, and mitigate corrosion or dissolution of the electrode, among other physical properties and advantages. In some embodiments, the methods 320, 440 described herein can be used to simultaneously coat the entire array of intra-body electrodes 578-1, 578-2, 578-3, 578-4, 527-1, 527-2, 527-3, 527-4 of the neurological apparatus 575, 525 and/or select electrodes of the array, simplifying manufacturer processing of the apparatus 575, which can similarly be applied to any of the apparatuses further illustrated herein, such as EP catheter 680, the cardiac apparatus 790, and/or the apparatus 899.

Each of the electrodes of the array can include a partial ring or segmented electrode, which can be used to produce shaped electrical fields. Although FIG. 5A illustrates a neurological apparatus 575 apparatus with four sets of four electrodes and FIG. 5B illustrates a neurological apparatus 575 with a one electrode, three electrodes, three electrodes, one electrode arrangement, examples are not so limited. In some embodiments, each electrode (and/or set or sub-sets thereof) can include a single ring electrode that extends around the circumference of the elongated conduit 577. Various embodiments can include least some of substantially the same features and attributes as described in: U.S. Pat. No. 10,245,429, issued Apr. 2, 2019, and entitled "METHODS AND APPARATUS FOR RENAL NEUROMODULATION", and U.S. Pat. No. 10,561,845, issued Feb. 18, 2020, and entitled "THERAPY ADJUSTMENT BASED ON PATIENT EVENT INDICATION", each of which are hereby incorporated by reference in their entirety for their general teachings related to neuromodulation, and their specific teachings related to example configurations of the neuromodulation devices. Examples of other suitable neuromodulation delivery configurations, deployment configurations and/or deployment mechanisms can be found in: U.S. Pat. No. 8,777,942, issued Jul. 15, 2014, and entitled "APPARATUS, SYSTEMS, AND METHODS FOR ACHIEVING INTRAVASCULAR, THERMALLY-INDUCED RENAL NEUROMODULATION"; U.S. Pat. No. 8,998,894, issued Apr. 7, 2015, entitled "CATHETER APPARATUSES HAVING MULTI-ELECTRODE ARRAYS FOR RENAL NEUROMODULATION AND ASSOCIATED SYSTEMS AND METHODS"; and U.S. Pat. No. 8,888,773, issued Nov. 18, 2014, and entitled "MULTI-ELECTRODE CATHETER ASSEMBLIES FOR RENAL NEUROMODULATION AND ASSOCIATED SYSTEMS AND METHODS," each of which are incorporated herein by reference in their entireties.

Figure 6:
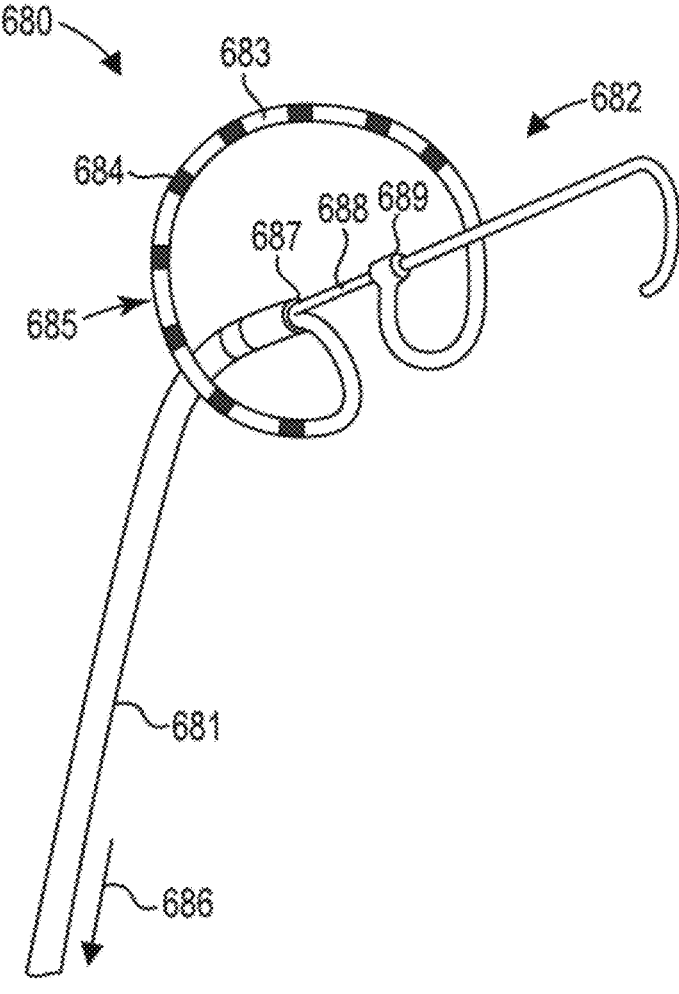

FIG. 6 illustrates an example cardiac apparatus that includes an intra-body electrode with a PEDOT-based coating, in accordance with embodiments of the present disclosure. For cardio implementations, such as for cardiac rhythm and heart failure diagnosis and/or treatment apparatuses, an array of electrodes can be used to record cardiac recordings and to provide electrical stimulation, as illustrated by the particular intra-body electrode 684.

The example apparatus illustrated by FIG. 6 can include an electrophysiology (EP) catheter 680. The EP catheter 680 can be used to map electrical activity of cardiac tissue which can be used to guide cardiac ablation procedure on the cardiac tissue. In some embodiments, the EP catheter 680 can itself perform the ablation. The EP catheter 680 can include an elongate conduit 681 having a distal portion 682 that is positionable with cardiac tissue of a user and proximal portion 686 which can be coupled to control circuitry. The elongate conduit 681 can include a flexible curved arm 685 with a plurality of intra-body electrodes on the flexible curved arm 685, as illustrated by the particular intra-body electrode 684. More particularly, the flexible curved arm 685 can include alternating regions of intra-body electrodes (formed by a coating of conductive material) and regions without intra-body electrodes, as shown by the particular region 683. One or more of the intra-body electrodes can include the PEDOT-based coating in accordance with the present disclosure. Electrical wires can be positioned within the elongate conduit 681 and the flexible curved arm 685 and can couple the control circuitry to the electrodes. In some embodiments, a first portion 687 of the arm 685 is coupled to the elongate conduit 681 and a second portion 689 is coupled to a guidewire sheath 688. The arm 685 can be transitioned from the configuration illustrated by FIG. 6 to a bundled configuration (not shown) when the sheath 688 is retracted or partially retracted for ablating purposes.

Examples are not limited to the particular EP catheter illustrated by FIG. 6. EP sensing and/or ablating devices can more generally include one or more intra-body electrodes at the distal portion. EP catheter devices can be used for diagnosis and/or therapy. For example, the electrodes can be used to sense electrical signals along the surface of the heart, which is sometimes referred to as "mapping". For EP mapping and other cardiac implementations, the PEDOT-based coating on the electrode(s) can allow for a reduced pacing threshold sufficient to reduce battery consumption and reduced pacing-after-polarization, and to increase signal-to-noise ratio sufficient to sense the cardiac signals. For example, one electrode cell can supervise the same amount of stimulation, resulting in lower current drain and lower battery consumption. Mapping can be performed by temporarily depolarizing selected tissue, with the responsive electrical activity being monitored for indication of local depolarization timing, refractory period duration, and/or any aberrant electrical activity. After mapping and diagnosing aberrant tissue, a physician can treat the patient by ablating the tissue, such as with the EP catheter itself. Combination mapping and ablation catheters can reduce the number of tasks for performing a treatment and increase accuracy, as the tissue to be ablated is identified and ablated without removing the catheter and positioning a separate ablation device. In some embodiments, one or more of the electrodes can act as a stimulation electrode that ablates the tissue using radio frequency energy and/or high-frequency pulses. Although examples are not so limited, and the ablation can be provided by other sources and/or can include a variety of energy modalities, including cryoablation, radio frequency (RF) ablation, and electroporation.

Various embodiments can include at least some of substantially the same features and attributes as described in: U.S. Pat. No. 10,426,377, issued Oct. 1, 2019, and entitled "DETERMINING A LOCATION OF A MEMBER"; U.S. Pat. No. 9,370,311, issued Jun. 21, 2016, and entitled "ELECTROPHYSIOLOGY CATHETER DESIGN", each of which are hereby incorporated by reference in their entirety for general teachings related to EP mapping and/or ablation, and their specific teachings related to example configurations of the EP catheter. Various embodiments can include at least some of substantially the same features and attributes as described in U.S. Pat. No. 5,967,978, issued Oct. 19, 1999, and entitled "INTRAVASCULAR SENSING DEVICE", which is hereby incorporated by reference in its entirety.

Figure 7:
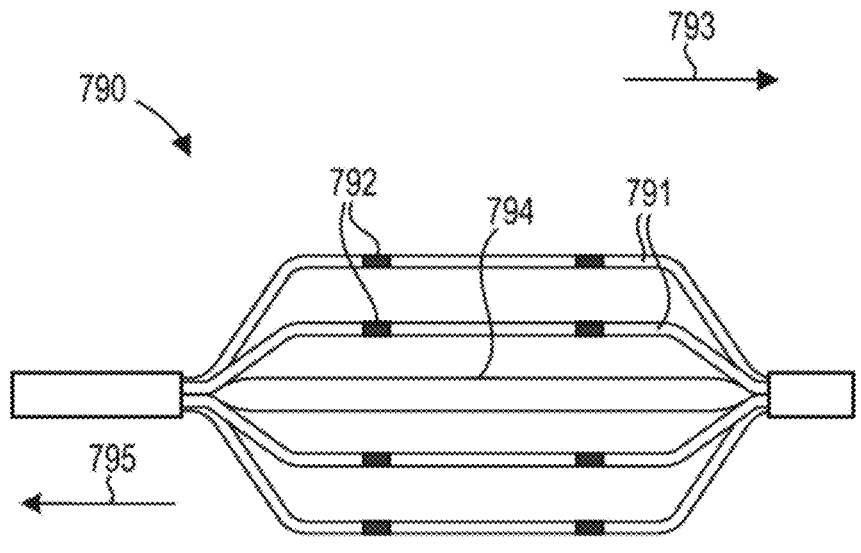

FIG. 7 illustrates another example cardiac apparatus that includes an intra-body electrode with a PEDOT-based coating, in accordance with embodiments of the present disclosure. In some embodiments, the cardiac apparatus 790 can include a three-dimensional (3D) EP mapping catheter. The 3D EP mapping catheter can include an elongate conduit 794 and a plurality of flexible arms 791 that extend from the elongate conduit 794 and are coupled to electrical wires and control circuitry on a proximal portion 795 of the apparatus 790. Each of the flexible arms 791 can include a plurality of intra-body electrodes 792 positioned toward or on a distal portion 793 of the apparatus 790 which are used to perform mapping, as described above. One or more of the plurality of intra-body electrodes 792 can include a PEDOT-based coating in accordance with the present disclosure.

However, embodiments are not limited to EP catheters and can include a variety of different cardiac apparatuses and other medical apparatus, including but not limited to, cardiac pacing leads, diabetes glucose sensors, leadless apparatuses, and drug-delivery apparatuses, among others. Various embodiments can include least some of substantially the same features and attributes as described in: U.S. Pat. No. 9,037,238, issued May 19, 2016, and entitled "METHOD FOR EFFICIENT DELIVERY OF DUAL SITE PACING; U.S. Pat. No. 6,021,340, issued Feb. 1, 2000, and entitled "GUIDING CATHETER FOR THE CORONARY SINUS"; U.S. Pat. No. 6,198,952, issued Mar. 6, 2001, and entitled "MULTIPLE LENS OXYGEN SENSOR FOR MEDICAL ELECTRICAL LEAD"; U.S. Pat. No. 6,163,723, issued Dec. 19, 2000, and entitled "CIRCUIT AND METHOD FOR IMPLANTABLE DUAL SENSOR MEDICAL ELECTRICAL LEAD", each of which are hereby incorporated by reference herein, in their entirety, for their general teaching related to sensing physiological signal and/or providing electrical stimulation, and for their specific teachings related to circuits and methods for sensing the physiological signals and/or providing electrical stimulation. Various embodiments can include least some of substantially the same features and attributes as described in: U.S. Pat. No. 5,509,411, issued Apr. 23, 1996, and entitled "INTRAVASCULAR SENSING DEVICE"; U.S. Pat. No. 5,699,796, issued Dec. 23, 1997, and entitled "HIGH RESOLUTION INTRAVASCULAR SIGNAL DETECTION"; U.S. Pat. No. 5,158,078, issued Oct. 27, 1997, and entitled "RATE RESPONSIVE PACEMAKER AND METHODS FOR OPTIMIZING ITS OPERATION"; and U.S. Pat. No. 5,144,949, issued Sep. 8, 1992, and entitled "DUAL CHAMBER RATE RESPONSIVE PACEMAKER WITH AUTOMATIC MODE SWITCHING", each of which are hereby incorporated herein by reference in their respective entireties.

In some embodiments, example apparatuses include a pacemaker-cardioverter-defibrillator (PCD). Various embodiments can include at least some of substantially the same features and attributes as described in: U.S. Pat. No. 5,545,186, issued Aug. 13, 1996, and entitled "PRIORI-TIZED RULE BASED METHOD AND APPARATUS FOR DIAGNOSIS AND TREATMENT OF ARRHYTHMIAS"; U.S. Pat. No. 5,354,316, issued Oct. 11, 1994, and entitled "METHOD AND APPARATUS FOR DETECTION AND TREATMENT OF TACHYCARDIA AND FIBRILLA-TION"; U.S. Pat. No. 5,314,430, issued May 24, 1994, and entitled "ATRIAL DEFIBRILLATOR EMPLOYING TRANSVENOUS AND SUBCUTANEOUS ELEC-TRODES AND METHODS OF USE"; U.S. Pat. No. 5,131, 388, issued Jul. 21, 1992, and entitled "IMPLANTABLE CARDIACE DEFIBILLATOR WITH IMPROVED CAPACITORS"; and U.S. Pat. No. 5,447,519, issued Sep. 5, 1995, and entitled "METHOD AND APPARATUS FOR DISCRIMINATION OF MONOMORPHIC AND POLY-MORPHIC ARRYTHMIAS AND FOR TREATMENT THEREOF", each of which are hereby incorporated herein by reference in their respective entireties.

Example apparatuses can be an implantable nerve stimu-lator or muscle stimulator and/or an implantable monitoring device, such as including at least some of substantially the same features and attributes as described in: U.S. Pat. No. 10,328,243, issued Jun. 25, 2019, and entitled "SYSTEM AND METHOD FOR POSITIONING IMPLANTABLE MEDICAL DEVICES WITHIN CORONARY VEINS"; U.S. Pat. No. 5,199,428, issued Apr. 6, 1993, and entitled "IMPLANTABLE ELECTRICAL NERVE STIMULATOR/ PACEMAKER WITH ISCHEMIA FOR DESCREASING CARDIAC WORKLOAD"; U.S. Pat. No. 5,207,218, issued May 4, 1993, and entitled "IMPLANTABLE PULSE GEN-ERATOR"; U.S. Pat. No. 5,330,507, issued Jul. 19, 1994, and entitled "IMPLANTABLE ELECTRICAL VAGAL STIMULATION FOR PREVENTION OR INTERRUP-TION OF LIFE THREATENING ARRHYTHMIAS"; and U.S. Pat. No. 5,331,966, issued Jul. 26, 1994, and entitled "SUBCUTANEOUS MULTI-ELECTRODE SENSING SYSTEM, METHOD AND PACER", each of which are hereby incorporated herein by reference in their entirety.

Figure 8:
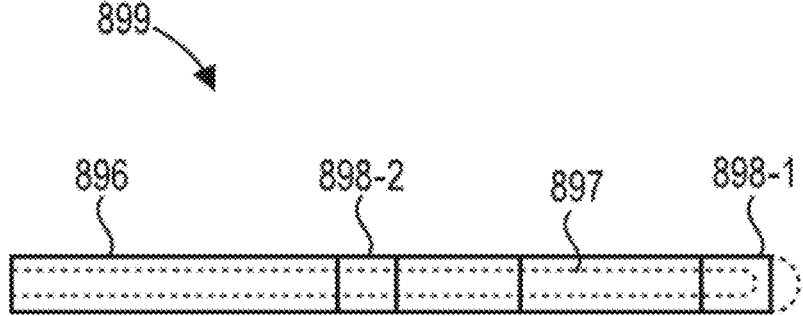

FIG. 8 illustrates an example apparatus that includes an intra-body electrode with a PEDOT-based coating, in accor-dance with embodiments of the present disclosure. More specifically, the example apparatus 899 includes two intra-body electrodes 898-1, 898-2 each with a PEDOT-based coating, with the two intra-body electrode 898-1, 898-2 being positioned on a surface of an elongate conduit 896. As shown, the elongate conduit 896 includes an internal cavity 897 in which the electrical wires can be positioned. Such an apparatus 899 can include and/or be implemented as a cardiac pacing lead, among other types of apparatuses such as those described above.

In various embodiments, circuitry, such as the above described control circuitry includes a processor and memory. The memory stores computer-readable instruc-tions, such as a program that is to be executed by the processor as a set of instructions. Example memory includes read-only memory (ROM), random-access memory (RAM), electrically erasable programmable read-only memory (EE-PROM), Flash memory, a solid state drive, and/or discrete data register sets. In some embodiments, the control cir-cuitry can include or otherwise have access to computer-readable instructions stored on the memory that includes instructions for monitoring the physiological signals and/or providing the electrical stimulation using an intra-body electrode, as described above.

It should be understood that various aspects disclosed herein may be combined in different combinations than the combinations specifically presented in the description and accompanying drawings. It should also be understood that, depending on the example, certain acts or events of any of the processes or methods described herein may be per-formed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

EXPERIMENTAL EMBODIMENTS

Various experiments were conducted to test example intra-body electrodes with the PEDOT-based coating in accordance with embodiments of the present disclosure. In some experimental embodiments, the PEDOT-based coating was formed on an electrode according to the method described by FIG. 4. FIGS. 9-13 provide various experi-mental data illustrating results, which are not intended to be limited and provided for illustrative purposes only.

Figure 9:
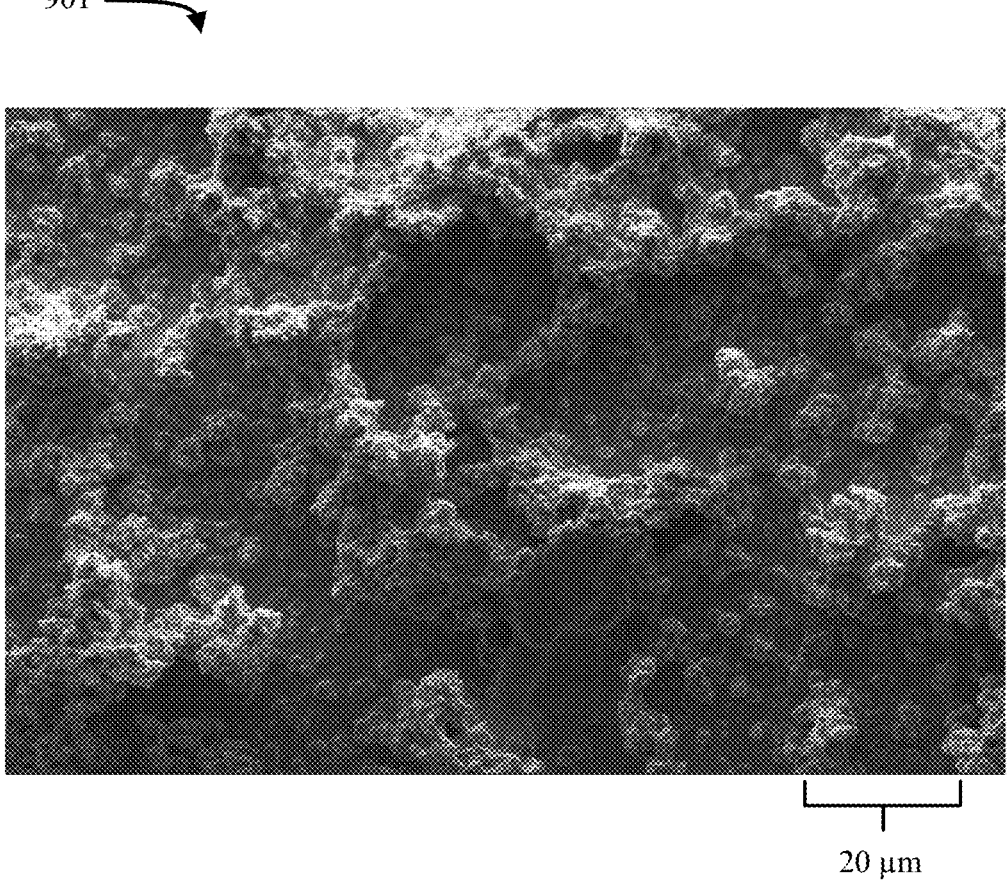
FIG. 9 is an image of an example PEDOT-based coating, in accordance with embodiments of the present disclosure.

FIG. 9 is an image of an example PEDOT-based coating, in accordance with embodiments of the present disclosure. More particularly, the image 901 includes a scanning elec-tron microscope (SEM) image of a generated PEDOT-based coating that includes a PEDOT:TFB structure cross-linked with a photoreactive polymer and a photoreactive-hydro-philic polymer.

FIGS. 10-13 are graphs illustrating example physical properties of intra-body electrodes with a PEDOT-based coating, in accordance with embodiments of the present disclosure.

Figure 10:
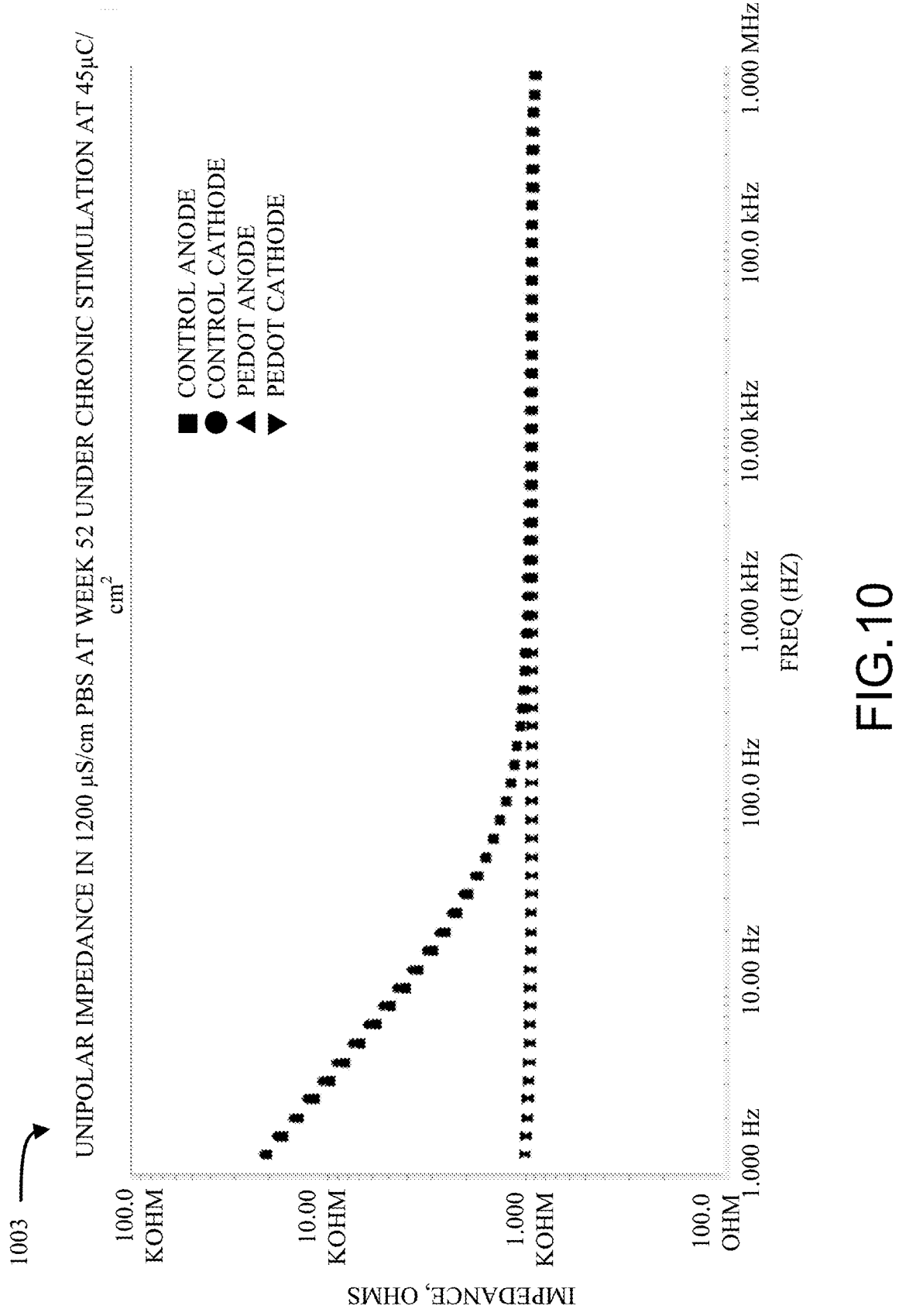

FIG. 10 illustrates an example graph 1003 showing rela-tive differences in impedance of electrodes with the PEDOT-based coating as compared to control electrodes without the PEDOT-based coating. The impedance measurements were made under a chronic electrical stimulation at forty five $\mu C/cm^2$ for fifty-two weeks in around twelve hundred micro-siemens per centimeter ($\mu S/cm$) phosphate-buffered saline (PBS). The chronic electrical stimulation at forty five $\mu C/cm^2$ stimulation includes or simulates an aggressive neuromodulation stimulation waveform. As shown by graph 1003, the electrodes with PEDOT-based coating exhibited lower impedance, and lower impedance difference, than the control electrodes, particularly at the frequency range of one Hz to one hundred Hz.

Figure 11:
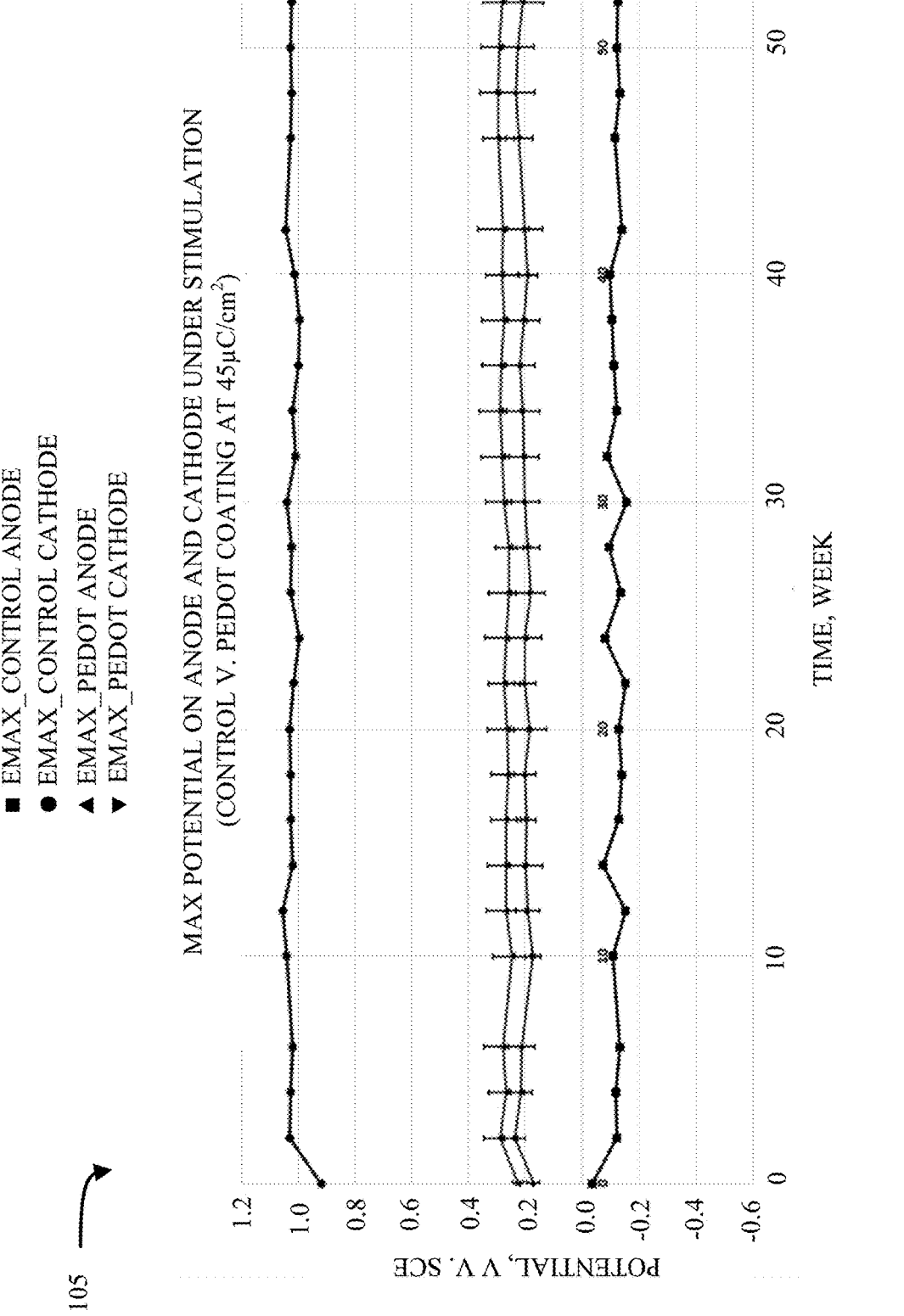

FIG. 11 illustrates a graph 1105 showing electrode polar-ization of electrodes with the PEDOT-based coating as compared to control electrodes without the PEDOT-based coating when under a chronic electrical stimulation at forty five $\mu C/cm^2$. As shown by graph 1105, the electrodes with the PEDOT-based coating minimized the electrode polar-ization, which can increase charge injection capacity, as compared to the control electrodes.

Figure 12:
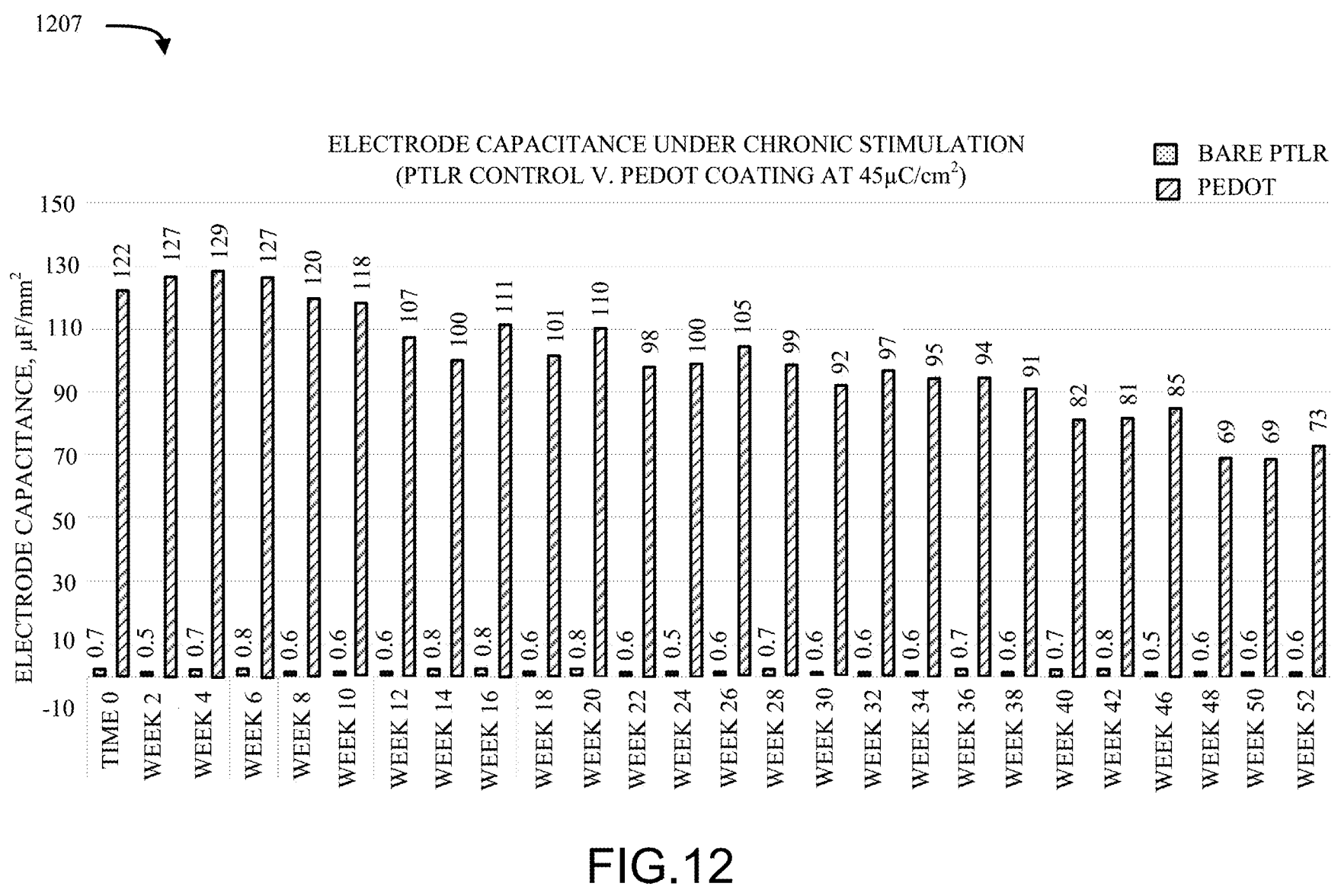

FIG. 12 illustrates a graph 1207 showing capacitance of electrodes with the PEDOT-based coating as compared to control electrodes without the PEDOT-based coating when under a chronic electrical stimulation at forty five $\mu C/cm^2$. The control electrodes included PtIr electrodes. In some embodiments, the electrodes with the PEDOT-based coating exhibited one hundred twenty-five times the capacitance of the PtIr electrodes.

Figure 13:
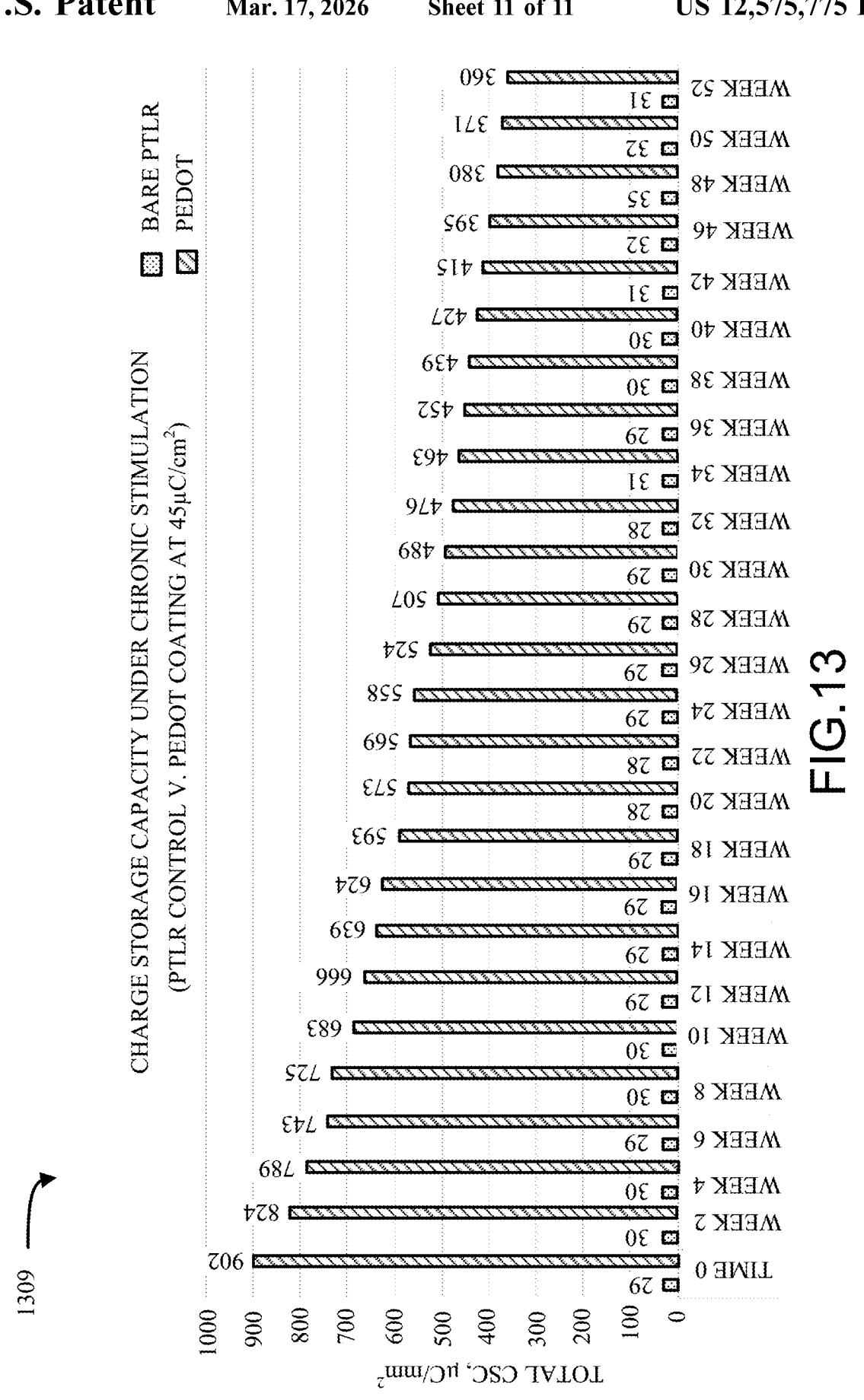

FIG. 13 illustrates a graph 1309 showing example charge storage capacity (CSC) of electrodes with the PEDOT-based coating as compared to control electrodes without the PEDOT-based coating when under a chronic electrical stimulation at forty five $\mu C/cm^2$. The control electrodes included PtIr electrodes. In some embodiments, the electrodes with the PEDOT-based coating exhibited nineteen times the CSC of the PtIr electrodes. The charge storage capacity and/or electrode potentials can be determined by cyclic voltammetry (CV), which is a three electrode measurement in which the potential of the WE with respect to the RE is swept at a constant predefined rate between two potential limits while allowing current to flow between the WE and the CE (e.g., the electrodes under test).

What is claimed is:

1. An apparatus, comprising:
an intra-body electrode; and
a poly(3,4-ethylenedioxythiophene) (PEDOT)-based coating on a surface of the intra-body electrode, the PEDOT-based coating including a PEDOT-backbone doped with tetrafluoroborate (TFB) counter ions and cross-linked to a photoreactive polymer and a photo-reactive-hydrophilic polymer;
wherein the intra-body electrode with the PEDOT-based coating is configured to provide a capacitance of at least sixty microfarad per square millimeter ($\mu F/mm^2$) and to exhibit a relative difference in impedance magnitude at ten kilohertz (kHz) and at ten Hz of five percent or less.

2. The apparatus of claim 1, further including an elongate conduit, wherein the intra-body electrode is positioned on an exterior surface of the elongate conduit.

3. The apparatus of claim 1, wherein the photoreactive polymer is non-charged and is configured to provide passivation against protein and cell adhesion when the intra-body electrode is implantable, and the intra-body electrode is configured to capture physiological signals.

4. The apparatus of claim 1, wherein the intra-body electrode includes a conductive material and the photoreactive-hydrophilic polymer is non-charged and is a hydrogel configured to provide lubricity and wettability to the PEDOT-based coating on the surface of the intra-body electrode.

5. The apparatus of claim 1, wherein the capacitance is at least seventy microfarad per square millimeter ($\mu F/mm^2$).

6. An apparatus, comprising:
an intra-body electrode; and
a poly(3,4-ethylenedioxythiophene) (PEDOT)-based coating on a surface of the intra-body electrode, the PEDOT-based coating including a PEDOT-backbone doped with tetrafluoroborate (TFB) counter ions, the intra-body electrode with the PEDOT-based coating configured to provide a charge storage capacity of at least 360 microcoulomb per square millimeter ($\mu C/mm^2$) and up to 902 $\mu C/mm^2$.

7. The apparatus of claim 6, wherein the intra-body electrode with the PEDOT-based coating is further configured to provide a total charge storage capacity of at least five hundred microcoulomb per square millimeter ($\mu C/mm^2$) and up to 902 microcoulomb per square millimeter ($\mu C/mm^2$).

8. The apparatus of claim 6, wherein the intra-body electrode with the PEDOT-based coating is further configured to maintain electrode potentials within a water stability window and minimize electrode polarization under electrical stimuli.

9. The apparatus of claim 6, further including:
an elongate conduit that carries electrically conductive wires; and
a plurality of intra-body electrodes positioned on an exterior surface of the elongate conduit and coupled to the electrically conductive wires, the plurality of intra-body electrodes including the intra-body electrode with the PEDOT-based coating and being configured to capture physiological signals and to deliver electrical signals.

10. The apparatus of claim 6, wherein the PEDOT-backbone doped with TFB counter ions is cross-linked to a photoreactive polymer and a photoreactive-hydrophilic polymer.

11. A method, comprising:
a. adding a layer of poly(3,4-ethylenedioxythiophene) (PEDOT)-based polymer on an intra-body electrode using a solution, the layer of PEDOT-based polymer including PEDOT doped with counter ions and cross-linked to a photoreactive polymer, wherein the counter ions include tetrafluoroborate (TFB);
b. incorporating a photoreactive-hydrophilic polymer with the layer of PEDOT-based polymer; and
c. curing the layer of PEDOT-based polymer to the photoreactive-hydrophilic polymer to form a PEDOT-based coating on the intra-body electrode, the PEDOT-based coating including the PEDOT doped with the counter ions and cross-linked to the photoreactive polymer and the photoreactive-hydrophilic polymer;
d. wherein the intra-body electrode with the PEDOT-based coating is configured to provide a capacitance of at least sixty microfarad per square millimeter ($\mu F/mm^2$) and to exhibit a relative difference in impedance magnitude at ten kilohertz (kHz) and at ten Hz of five percent or less.

12. The method of claim 11, wherein incorporating the photoreactive-hydrophilic polymer with the layer of PEDOT-based polymer includes dip coating the intra-body electrode with the layer of PEDOT-based polymer in a solution that includes the photoreactive-hydrophilic polymer dissolved in a solvent.

13. The method of claim 11, wherein curing the layer of PEDOT-based polymer to the photoreactive-hydrophilic polymer includes exposing the layer of PEDOT-based polymer with the incorporated photoreactive-hydrophilic polymer on the intra-body electrode to ultraviolet light for a period of time.

14. The method of claim 11, further including curing an additional amount of the photoreactive polymer to the layer of PEDOT-based polymer.

15. The method of claim 11, further including forming the solution by dissolving a 3,4-ethylenedioxythiophene (EDOT) monomer in a solvent, wherein the solution includes the EDOT monomer, the photoreactive polymer, the counter ions, and the solvent.

16. The method of claim 12, wherein the solution includes tetrabutylammonium tetrafluoroborate (TBATFB), and the solvent includes acetonitrile, and the PEDOT-based coating includes a PEDOT:TFB structure cross-linked to the photoreactive polymer and the photoreactive-hydrophilic polymer.

17. The method of claim 11, wherein adding the layer of PEDOT-based polymer includes electrochemically depositing the PEDOT doped with the counter ions on a surface of the intra-body electrode using the solution, wherein the PEDOT doped with the counter ions on the surface of the intra-body electrode includes a PEDOT:tetrafluoroborate (TFB) structure that passively incorporates the photoreactive polymer.

18. The method of claim 17, wherein electrochemically depositing the layer includes depositing the PEDOT doped with the counter ions using potentiostatic electrochemical deposition by applying a voltage for a period of time to the intra-body electrode while the intra-body electrode is submerged in the solution.

19. The method of claim 17, wherein electrochemically depositing the layer includes depositing the PEDOT doped with the counter ions using cyclic voltammetry between a voltage range and at a scan rate for a number of cycles.

20. The method of claim 17, further including curing the PEDOT doped with the counter ions to the passively incorporated photoreactive polymer to form the layer of PEDOT-based polymer including the PEDOT doped with the counter ions cross-linked to the photoreactive polymer.

* * * * *